United States Patent [19]

Budin

[11] Patent Number: 5,821,437

[45] Date of Patent: Oct. 13, 1998

[54] ENVIRONMENTAL LIQUID COLLECTION APPARATUS

[76] Inventor: Timothy M. Budin, 11523 S. 60th St., Omaha, Nebr. 68133

[21] Appl. No.: 775,948

[22] Filed: Jan. 3, 1997

[51] Int. Cl.$^6$ ..................................................... G01N 1/10
[52] U.S. Cl. ..................................... 73/864.63; 73/864.67; 73/864.66; 220/253; 220/262
[58] Field of Search ........................... 73/864.66, 864.63, 73/864.51, 864, 863.02, 864.67, 864.91; 220/202, 253, 262, 335, 336

[56] References Cited

U.S. PATENT DOCUMENTS

| | | | |
|---|---|---|---|
| 2,314,372 | 3/1943 | Spilhaus | 137/18 |
| 2,388,548 | 11/1945 | Jurs, Jr. | 137/18 |
| 3,379,065 | 4/1968 | Gibbon | 73/425.4 |
| 4,027,538 | 6/1977 | Snyder et al. | 73/425.4 R |
| 4,266,429 | 5/1981 | Brovold | 73/864.63 |
| 4,949,582 | 8/1990 | Vollweiler | 73/864.63 |
| 4,958,528 | 9/1990 | Garrison | 73/864.63 |
| 5,487,314 | 1/1996 | Phillips | 73/864.65 |
| 5,524,495 | 6/1996 | Dudley | 73/863.52 |

FOREIGN PATENT DOCUMENTS

| | | | |
|---|---|---|---|
| 1249381 | 8/1986 | Russian Federation | 73/864.66 |
| 1656385 | 6/1991 | Russian Federation | 73/864.66 |
| 2236522 | 4/1991 | United Kingdom | 73/864.63 |

*Primary Examiner*—Hezron E. Williams
*Assistant Examiner*—Nashmiya Fayyaz
*Attorney, Agent, or Firm*—Zarley, McKee, Thomte Voorhees & Sease; Mark D. Frederiksen

[57] ABSTRACT

A liquid collection apparatus includes a container for storing a liquid sample removably connected to a lid. The lid includes an opening therethrough to permit liquid to pass into the container for storage. A closure disk is operably mounted on the lid to selectively close the opening after a predetermined amount of liquid has entered the container. The closure disk is biased towards the closed position, and is retained in an open position by an operable latch which is connected to the bottom of the lid. A trigger operably mounted on the bottom of the lid has a float connected thereto which will pivot a trigger arm as the level of liquid within the container raises, thereby operating the latch to disengage from the closure disk and permit the closure disk to rotate to a closed position, thereby sealing the sample within the container. The container is supported in an upright orientation within a holder frame which is selectively and adjustably mounted to a ground engaging post, thereby permitting the container to be positioned at the desired position above the ground.

18 Claims, 5 Drawing Sheets

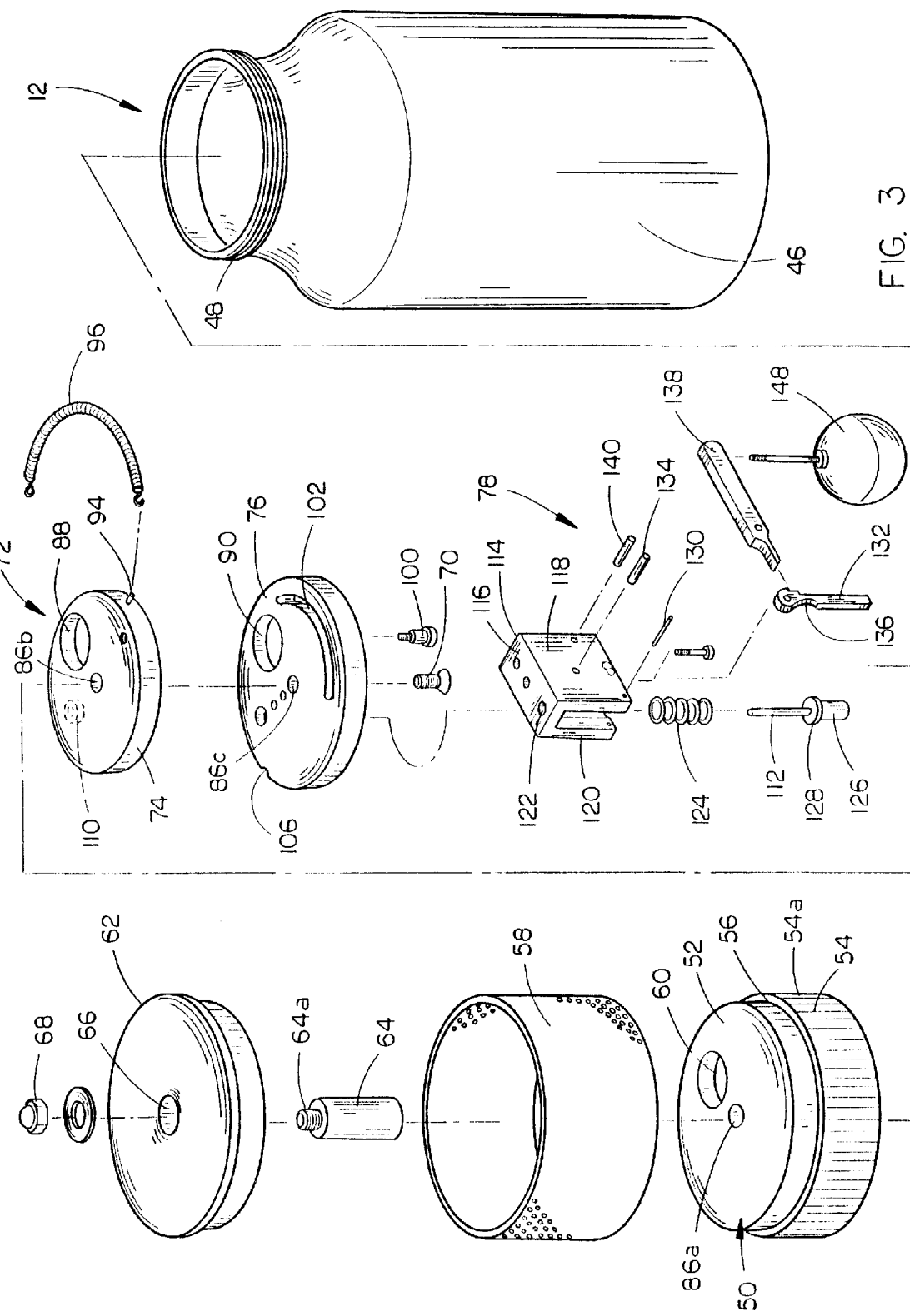

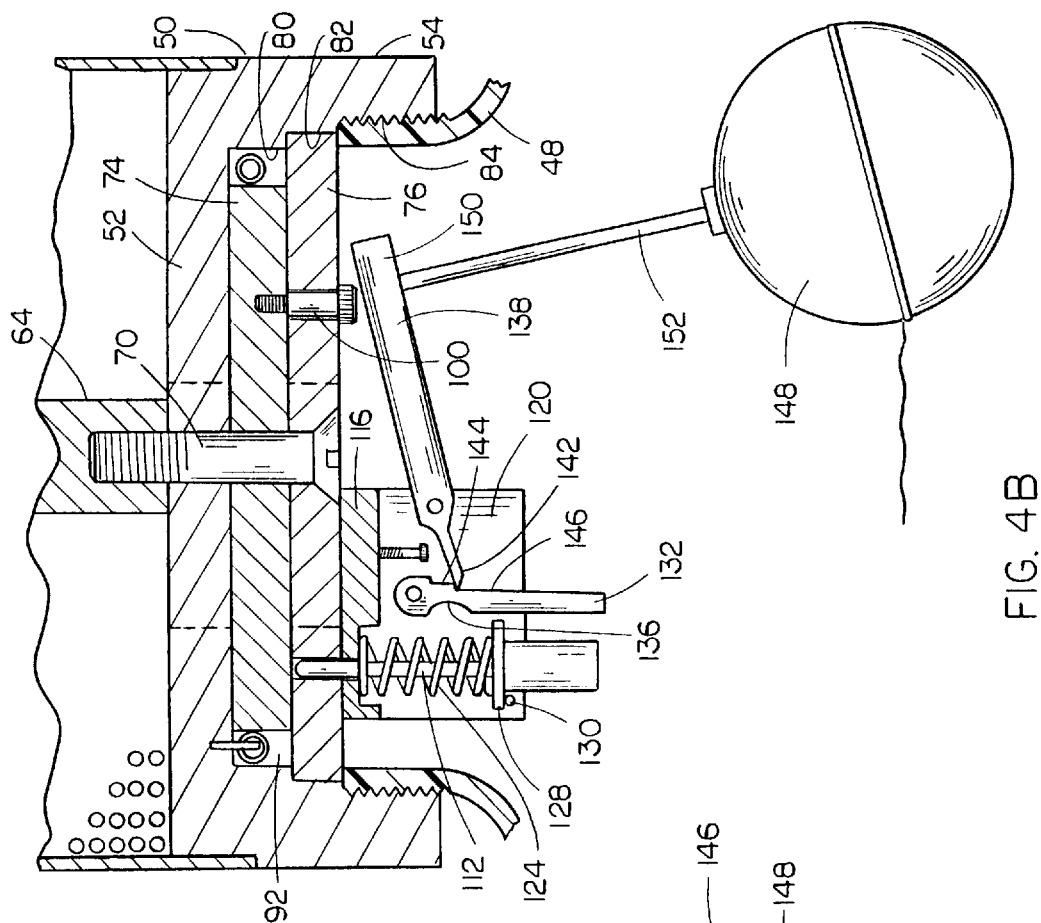
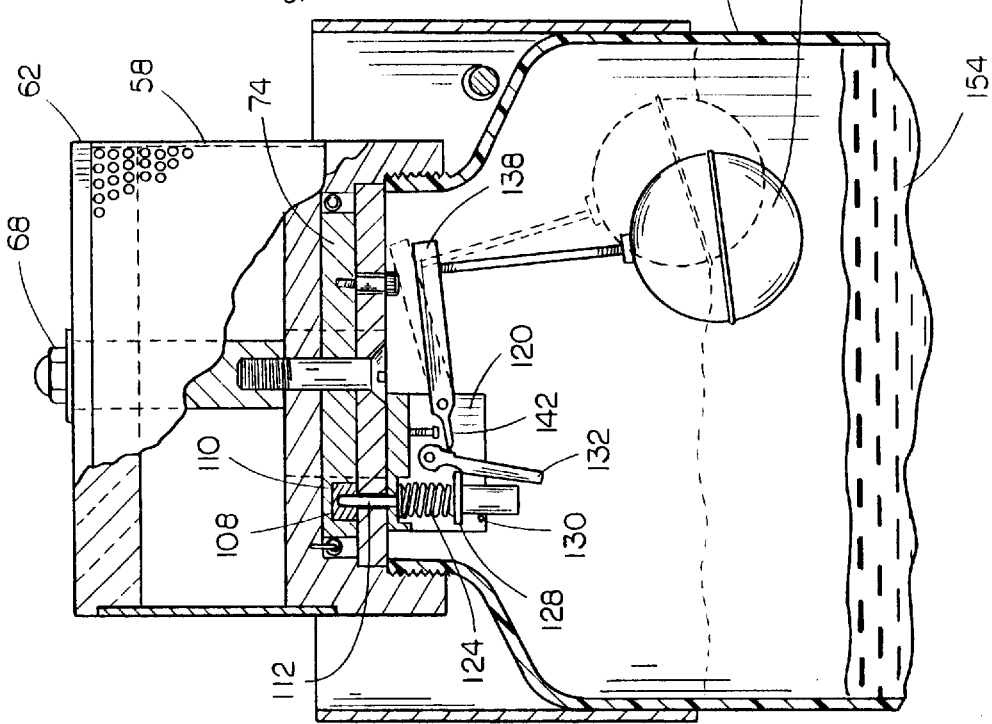
FIG. 4B
FIG. 4A

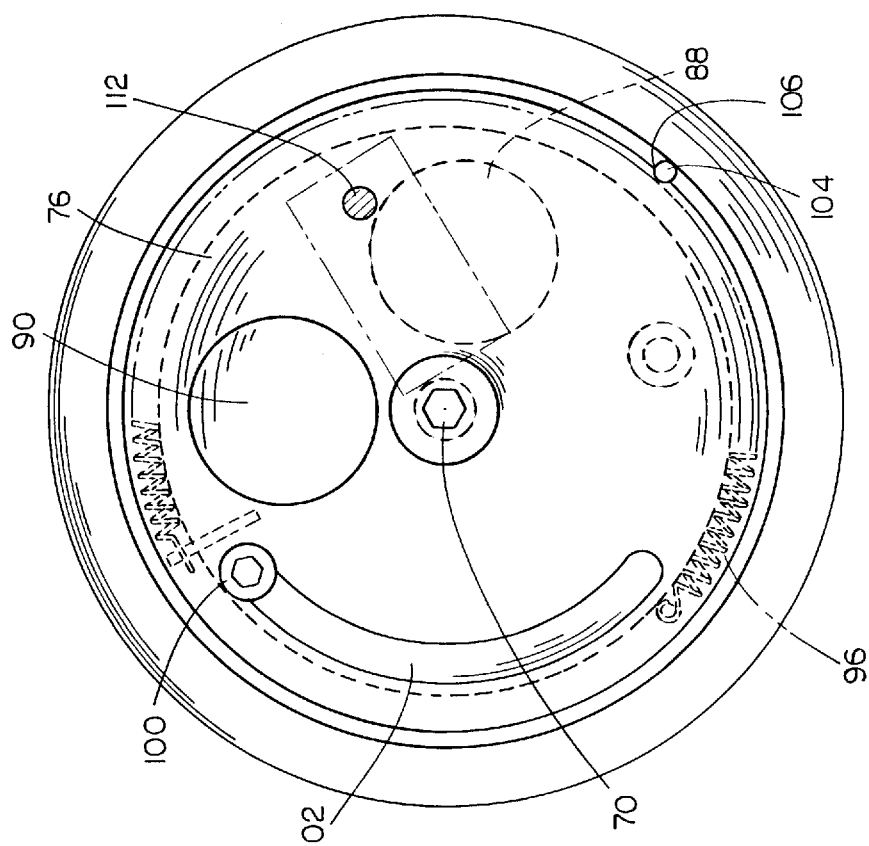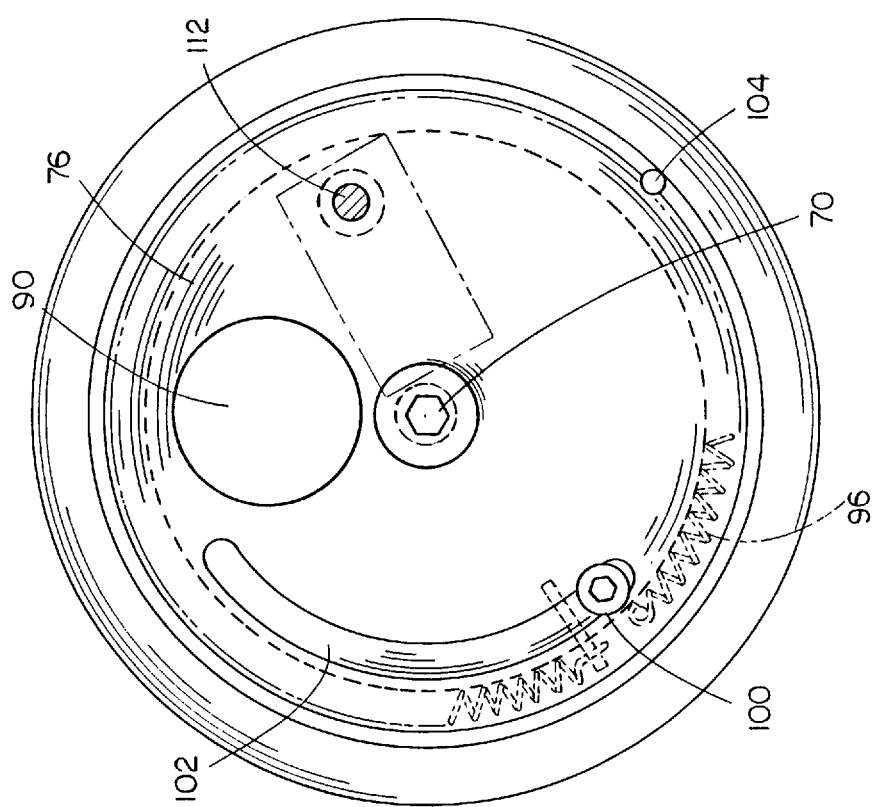

ENVIRONMENTAL LIQUID COLLECTION APPARATUS

TECHNICAL FIELD

The present invention relates generally to apparatus for collecting liquids, and more particularly to an improved water sampler for collecting a true first sample of liquid at a sampling location with a mechanical trigger for sealing the sample within a container.

BACKGROUND OF THE INVENTION

Testing for pollution of water has become a common requirement for various industries, including landfills, farm acreages, and commercial industry. In order to comply with various Environmental Protection Agency (EPA) regulations, testing of run off water from various sites has become a legal requirement.

In order to comply with the various EPA regulations, it is common for industry to utilize very expensive instrumentation which are electrically powered and left at a particular site location, to transmit data to a computer or other storage apparatus. Because most prior art electronic apparatus are cost prohibitive, there is a need for simple mechanical water sampling apparatus to permit repeated testing of run off water from various remote locations.

SUMMARY OF THE INVENTION

It is therefore a general object of the present invention to provide an improved liquid collection apparatus for collecting a true first sample of liquid from a sampling location.

Another object is to provide an improved liquid collection apparatus which does not require a power source of any type.

Still another object of the present invention is to provide an improved liquid collection apparatus which may be adjusted at a site location to collect a sample of water from a predetermined portion of run off water.

Yet a further object is to provide a liquid collection apparatus which is simple and economical to manufacture, and easy to use.

These and other objects of the present invention will be apparent to those skilled in the art.

The liquid collection apparatus of the present invention includes a container for storing a liquid sample removably connected to a lid. The lid includes an opening therethrough to permit liquid to pass into the container for storage. A closure disk is operably mounted on the lid to selectively close the opening after a predetermined amount of liquid has entered the container. The closure disk is biased towards the closed position, and is retained in an open position by an operable latch which is connected to the bottom of the lid. A trigger operably mounted on the bottom of the lid has a float connected thereto which will pivot a trigger arm as the level of liquid within the container raises, thereby operating the latch to disengage from the closure disk and permit the closure disk to rotate to a closed position, thereby sealing the sample within the container. The container is supported in an upright orientation within a holder frame which is selectively and adjustably mounted to a ground engaging post, thereby permitting the container to be positioned at the desired position above the ground.

BRIEF DESCRIPTION OF THE DRAWINGS

FIG. 3 is an exploded perspective view of the collector;

FIG. 4A is a sectional view through a portion of the collector showing the container closure apparatus;

FIG. 4B is an enlarged sectional view similar to FIG. 4A but with the float trigger moved to a second "sealed" position;

FIG. 5A is a bottom view of the lid showing the rotary closure disk in the "open" position;

FIG. 5B is a bottom view of the lid with the closure disk moved to a "closed" position;

DESCRIPTION OF THE PREFERRED EMBODIMENT

Figure 1:
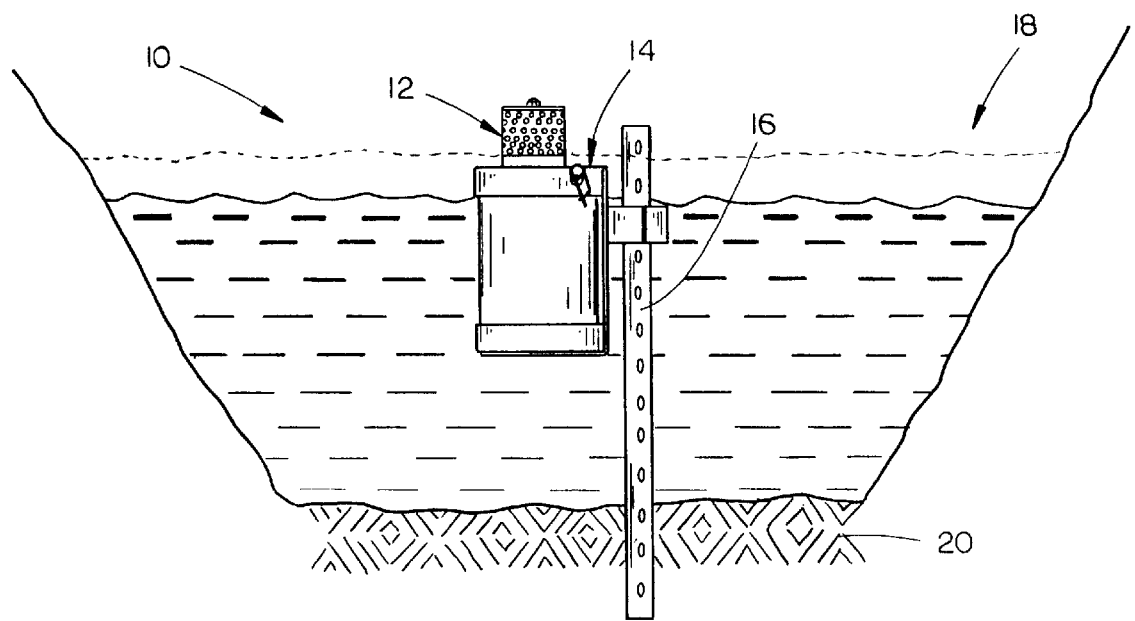
FIG. 1 is a side elevational view of the apparatus installed in a stream bed.

Referring now to the drawings, in which similar or corresponding parts are identified with the same reference numeral and more particularly to FIG. 1, the liquid collection apparatus of the present invention is designated generally at 10 and includes a collector 12 removably installed in a collector holder 14, which is in turn adjustably mounted on a support post 16. As shown in FIG. 1, the liquid collection apparatus 10 may be installed within a stream 18 with post 16 driven into the stream bed 20 and holder 14 positioned on post 16 such that collector 12 is supported at the desired level above stream bed 20.

Figure 2:
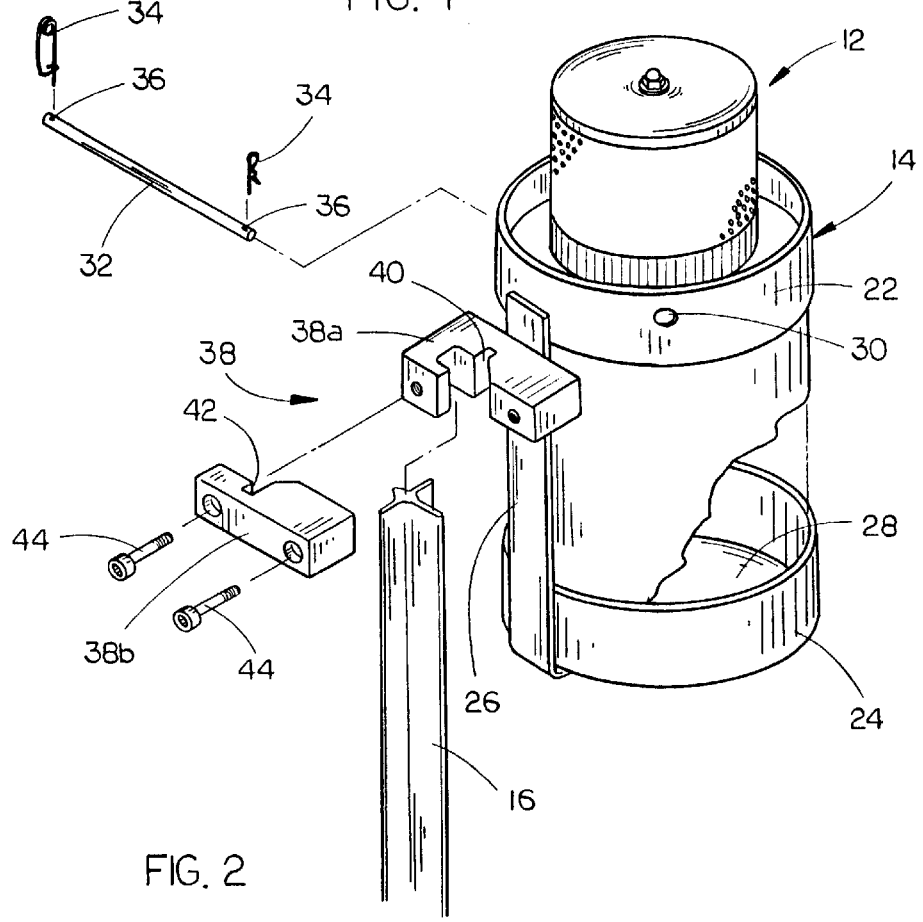
FIG. 2 is a perspective view of the collector with an exploded view of the collector support.

Referring now to FIG. 2, holder 14 includes an upper ring 22 and lower ring 24 connected by a strap 26 in vertically spaced apart and coaxial relationship. A plate 28 is mounted across the interior of lower ring 24 to form a bottom for holder 14 to support collector 12. A pair of coaxial apertures 30 are formed in upper ring 22 to receive a rod 32 therethrough for preventing escape of the collector 12 upwardly out of holder 14. Rod 32 has a length such that it will project outwardly from upper ring 22 when journaled through apertures 30. A pair of cotter pins 34 are selectively journaled through openings 36 in the ends of rod 32 to selectively secure rod 32 in the apertures of ring 22.

The base 38a of a two piece clamp 38 is affixed to strap 26 and has a slot 40 formed therein for receiving a portion of post 16 therein. The head 38b of clamp 38 also includes a slot 42 for receiving a portion of post 16 therein, such that post 16 is enclosed between the base 38a and head 38b of clamp 38 when the head 38b is secured to the base 38a with fasteners 44. Fasteners 44 are preferably screws or the like which may be selectively tightened and loosened to permit vertical adjustment of clamp 38 along the height of post 16, to thereby position collector 12 at a desired level.

Referring now the FIG. 3, collector 12 includes a collection container 46 of a conventional variety having an exteriorly threaded mouth 48. A lid 50 is provided for selective securement on mouth 48, and includes a disk-shaped plate 52 with a depending perimeter wall 54. A shoulder 56 is formed in the upper end of the exterior face 54a of perimeter wall 54, which will receive the lower end of a cylindrical screen 58 thereon. An opening 60 in plate 52 provides access to the interior of container 46, as described in more detail hereinbelow. Screen 58 will prevent the entry of sticks, rocks, and other debris having a size greater than the aperture size of the screen 58.

A cover 62 is secured over the top of screen 58 to enclose the open upper end of screen 58, and thereby force all liquids to pass through the screen before entering opening 60. A stand-off 64 has a threaded upper end 64a which is journaled through a hole 66 in cover 62, upon which a nut 68 is secured to retain cover 62 on the end of stand-off 64. The lower end of stand-off 64 has an interiorly threaded aperture therein which will receive a securement screw 70 (shown in FIG. 4B) as described in more detail hereinbelow. Lid 50 has a mechanical closure mechanism 72 attached thereto which is operable to open or close opening 60 in lid plate 52, to selectively permit the entry of a water sample into a container 46 attached to lid 50. Mechanical closure mechanism 72 includes a rotary closure disk 74, a disk-shaped cover plate 76, and a trigger release mechanism designated generally at 78.

As shown in FIG. 4B, the depending wall 54 of lid 50 has three stepped surfaces formed on its interior face. The upper cylindrical surface 80 forms a disk-shaped depression in conjunction with the bottom face of lid plate 52, which will receive closure disk 74 therein. Intermediate surface 82 has a greater diameter than upper surface 80, and receives cover plate 76 therein. Finally, lower interior surface 84 of lid wall 54 has a greater diameter than intermediate interior surface 82, and is threaded to receive the threaded mouth 48 of the container thereon.

Referring once again to FIG. 3, the lid plate 52, closure disk 74, and cover plate 76, each have a central aperture 86a, 86b, and 86c, respectively, therethrough, aligned to receive securement screw 70 therethrough. Securement screw 70 is threaded into the lower end of stand-off 64 to retain the lid 50, disk 74, and plate 76 operably connected together. Disk 74 and closure plate 76 each have an opening 88 and 90 respectively which will permit the entry of a water sample into container 46 when aligned with opening 60 in lid 50.

As discussed in more detail hereinbelow, disk 74 is rotatable on securement screw 70 between an "open" position with opening 88 aligned with openings 60 and 90 in lid 50 and cover plate 76, and a "closed" position with opening 88 rotated out of alignment with openings 60 and 90, to prevent the passage of liquid into container 46.

Figure 6A:
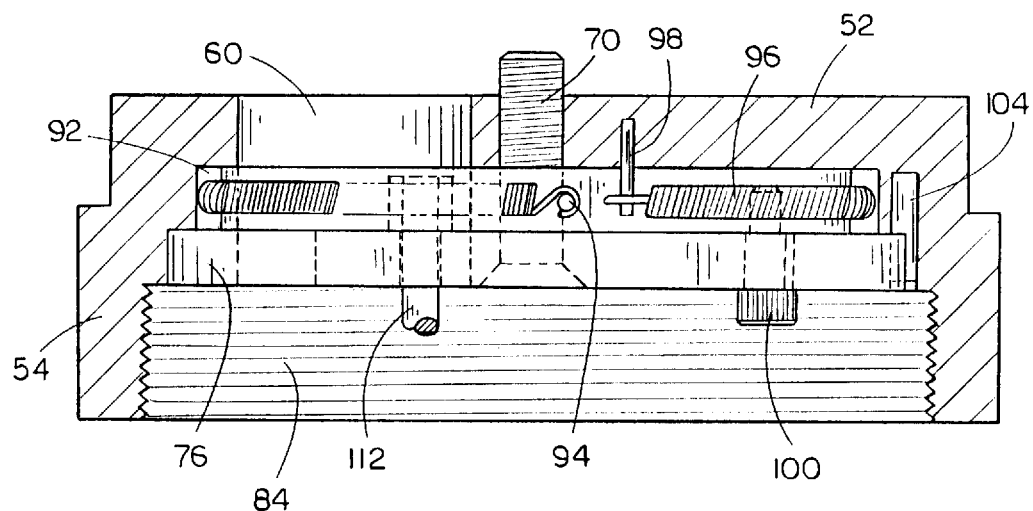
FIG. 6A is a sectional view through the lid with the closure disk, cover plate, and related components shown in side elevational view, the closure disk positioned in the "open" position.
Figure 6B:
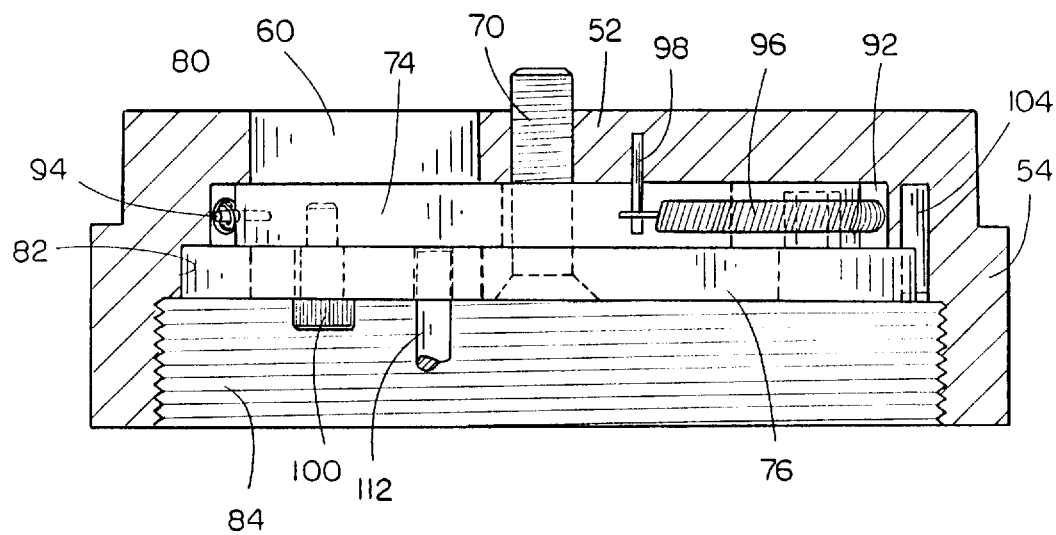
FIG. 6B is a view similar to FIG. 6A, but with the closure disk rotated to a "closed" position.

Referring now to FIGS. 4B and 6B, it can be seen that rotary closure disk 74 has a diameter less than that of the lid wall upper interior surface 80 so as to form an annular channel 92 therebetween. A pin 94 projecting outwardly from the circumferential surface of disk 74 retains one end of a coil spring 96 within channel 92. A second pin 98 depends from the bottom surface of lid plate 52 into channel 92, and retains the opposite end of spring 96. Spring 96 thereby extends from the first pin 94 to the second pin 98 around the circumference of disk 74 within channel 92, and will serve as a biasing force to rotate disk 74 to the "closed" position.

As shown in FIGS. 3, 4B, 5B and 6B, cover plate 76 has a diameter greater than the diameter of the upper interior surface 80 of lid wall 54, so as to enclose closure disk 74 between cover plate 76 and lid plate 52. Disk 74 is really rotatable on securement screw 70 to permit rotation between cover plate 76 and lid plate 52. A peg 100 depends from the bottom face of disk 74, for rotation therewith, and is journaled through an arcuate slot 102 formed in cover plate 76. Slot 102 is curved at a constant radius measured from the center of the securement screw 70 such that peg 100 will travel one end of slot 102 to the other end of slot 102 as the disk 74 travels between the open and closed positions. The ends of slots 102 stop rotation of disk 74 in each of the open and closed positions.

A key pin 104 depends from lid wall 54 and engages a groove 106 in the circumferential surface of cover plate 76, as to prevent rotation of cover plate 76. The bottom of disk 74 has a well 108 formed therein, lined with a bushing 110 which will receive a release pin 112 therein to selectively hold the disk 74 in the open position, as shown in FIG. 4A.

Referring now to FIGS. 3, 4A, and 4B, release mechanism 78 includes a generally U-shaped bracket 114 having a base 116 bolted to the bottom of cover plate 76, with a pair of legs 118 and 120 depending from base 116. Release pin 112 is slidably journaled through a hole 122 in base 116 and has a coil spring 124 surrounding the pin and located between legs 118 and 120 of bracket 114. The lower end of release pin 112 includes a head 126 with an outwardly projecting flange 128 thereon. Spring 124 extends between base 116 and flange 128, surrounding pin 112, to thereby bias release pin 112 downwardly out of engagement with bushing 110. A stop pin 130 extending between legs 1 18 and 120 in the downward path of flange 128, prevents release pin 112 from being biased downwardly beyond a "release" position, shown in FIG. 4B.

A latch arm 132 is pivotally mounted on a pivot pin 134 between legs 118 and 120 of bracket 114. Latch arm 132 has a hook portion 136 formed along one side thereof to selectively engage and retain flange 128 of release pin 112 in the "engaged" position with spring 124 compressed, and the upper end of release pin 112 engaged within bushing 110. Release pin 112 and latch arm 132 are shown in the "engaged" positions in FIG. 4A. Pivotal movement of latch arm 132 away from flange 128, as shown in FIG. 4B, permits spring 124 to bias flange 128 downwardly, thereby moving release pin 112 to the "disengaged" position, releasing disk 74, and thereby permitting disk 74 to rotate into the "closed" position.

Because hook portion 136 is a curved surface, flange 128 will continuously be biased downwardly, pushing latch arm 132 outwardly towards the "disengaged" or "released" position. Latch arm 132 is selectively maintained in the "engaged" position by a trigger arm 138 pivotally connected between bracket legs 118 and 120 on a pivot pin 140. Trigger arm 138 includes a forward end 142 which will engage either an upper step 144 or a lower step 146 on latch arm 132, to retain latch arm 132 in either the engaged position or disengaged position, respectively. As shown in FIGS. 4A and 4B, pivotal movement of trigger arm 138 will move forward portion 142 from upper step 144 to lower step 146, thereby permitting latch arm 132 to pivot from the engaged position to the disengaged position.

A float 148 is connected to a rearward end 150 of trigger arm 138, by a float rod 152 threaded into an aperture in trigger arm 138. As shown in FIG. 4A, float 148 is of sufficient weight to retain trigger arm 138 in the engaged position to maintain latch arm 132 and release pin 112 in the engaged position. As the liquid 154 within container 146 rises, float 148 will be forced upwardly to pivot trigger arm 138, thereby releasing latch arm 132 and release pin 112, as shown in FIG. 4B. The release of latch arm 132 and release pin 112 permits the rotation of disk 74, to thereby seal the container 146 and prevent any further liquid from entering the container. The float rod 152 may be replaced with a rod of any predetermined length, to permit the user to determine the amount of liquid sample to be retained within container 146.

Whereas the liquid collection container of present invention has been shown and described in connection with the preferred embodiment thereof, many modifications, substitutions and additions may be made which are within the intended broad scope of the appended claims.

I claim:

1. A liquid sample collection apparatus, comprising:

a sample container having an open mouth at an upper end for collecting a liquid sample;

a lid removably connected to the container mouth, for selectively closing the container mouth;

said lid having an opening therethrough for the passage of liquid sample into the container;

a closure disk operably connected to the lid for movement between a first "closed" position covering the lid opening to prevent liquid passage therethrough, and a second "open" sampling position oriented so as to reveal at least a portion of the lid opening;

biasing means connected to the closure disk, for urging the disk from the "open" position to the "closed" position;

an operable latch connected to the lid and operable between an engaged position holding the disk in the "open" position against the force of the biasing means, and a disengaged position out of contact with the disk permitting the disk to rotate to the "closed" position; and a trigger connected to the lid, operable between a first position retaining the latch in the engaged position and a second position releasing the latch from the first trigger position.

2. The apparatus of claim 1, wherein said lid includes a generally disk-shaped plate with a wall depending from a circumferential edge of the plate, said wall including an interior surface threaded to engage an exteriorly threaded portion of the container mouth, said lid opening formed in the lid plate and said disk, latch and trigger connected to a bottom surface of the lid plate and positioned within the container.

3. A liquid sample collection apparatus, comprising:

a sample container having an open mouth at an upper end for collecting a liquid sample;

a lid removably connected to the container mouth, for selectively closing the container mouth;

said lid having an opening therethrough for the passage of liquid sample into the container;

a closure disk operably connected to the lid for movement between a first "closed" position covering the lid opening to prevent liquid passage therethrough, and a second "open" sampling position oriented so as to reveal at least a portion of the lid opening;

biasing means connected to the closure disk, for urging the disk from the "open" position to the "closed" position:

an operable latch connected to the lid and operable between an engaged position holding the disk in the open position against the force of the biasing means, and a disengaged position out of contact with the disk permitting the disk to rotate to the closed position; and a trigger connected to the lid, operable between a first position retaining the latch in the engaged position and a second position releasing the latch from the first trigger position;

said lid including a generally disk-shaped plate with a wall depending from a circumferential edge of the plate, said wall including an interior surface threaded to engage an exteriorly threaded portion of the container mouth;

said lid opening formed in the lid plate;

said disk, latch and trigger connected to a bottom surface of the lid plate and positioned within the container;

said closure disk being rotatably mounted to the bottom of the lid plate, and said closure disk including an opening therein aligned with the lid opening when the closure disk is in the open position, and misaligned from the lid opening when in the closed position.

4. The apparatus of claim 3, wherein the biasing means is connected between the disk and the lid, to urge the disk to rotate to the closed position.

5. The apparatus of claim 4, wherein said trigger includes a trigger arm pivotally mounted on the bottom of the lid with a forward portion pivotable between a first position in contact with the latch and retaining the latch in the engaged position, and a second position pivoted out of engagement with the latch, to release the latch from the engaged position.

6. The apparatus of claim 5, further comprising means on the trigger arm for selectively pivoting the arm in response to liquid level within the container.

7. The apparatus of claim 6, wherein said means for selectively pivoting the trigger arm includes a float on a float rod, the float rod removably connected to a rearward end of the trigger arm.

8. The apparatus of claim 7, further comprising a screen projecting upwardly from a top surface of the lid, surrounding the lid opening, and a cover extending across an upper end of the screen to secure the screen and enclose the lid opening within the perimeter of the screen.

9. The apparatus of claim 8, further comprising a ground engaging support post for supporting the container at a predetermined level relative to the ground, and a holder adjustably mounted on the post for selective vertical adjustment along the post, said container removably secured in said holder.

10. The apparatus of claim 9, wherein the holder includes a frame with upper and lower ends, the upper end open to selectively receive the container, and the lower end including a bottom to support a lower end of the container, said frame adjustably mounted on the post to retain the container in an upright orientation and further comprising means for selectively securing the container within the holder to prevent upwardly movement of the container out of the upper end of the holder.

11. The apparatus of claim 10, wherein said frame includes an operable clamp adjustably securing the holder to the post, the clamp operable between a "clamped" position selectively securing the holder in a desired position on the post and an "unclamped" position, permitting vertical movement of the holder along the post.

12. The apparatus of claim 1, wherein said trigger includes a trigger arm pivotally mounted on the bottom of the lid with a forward portion pivotable between a first position in contact with the latch and retaining the latch in the engaged position, and a second position pivoted out of engagement with the latch, to release the latch from the engaged position.

13. A liquid sample collection apparatus, comprising:

a sample container having an open mouth at an upper end for collecting a liquid sample;

a lid removably connected to the container mouth, for selectively closing the container mouth;

said lid having an opening therethrough for the passage of liquid sample into the container;

a closure disk operably connected to the lid for movement between a first "closed" position covering the lid opening to prevent liquid passage therethrough, and a second "open" sampling position oriented so as to reveal at least a portion of the lid opening;

biasing means connected to the closure disk, for urging the disk from the open position to the closed position;

an operable latch connected to the lid and operable between an engaged position holding the disk in the open position against the force of the biasing means, and a disengaged position out of contact with the disk permitting the disk to rotate to the closed position;

a trigger connected to the lid, operable between a first position retaining the latch in the engaged position and a second position releasing the latch from the first trigger position;

said trigger including a trigger arm pivotally mounted on the bottom of the lid with a forward portion pivotable between a first position in contact with the latch and retaining the latch in the engaged position, and a second position pivoted out of engagement with the latch, to release the latch from the engaged position; and means on the trigger arm for selectively pivoting the arm in response to liquid level within the container.

14. The apparatus of claim 7, wherein said means for selectively pivoting the trigger arm includes a float on a float rod, the float rod removably connected to a rearward end of the trigger arm.

15. A liquid sample collection apparatus, comprising:

a sample container having an open mouth at an upper end for collecting a liquid sample;

a lid removably connected to the container mouth, for selectively closing the container mouth;

said lid having an opening therethrough for the passage of liquid sample into the container;

a closure disk operably connected to the lid for movement between a first "closed" position covering the lid opening to prevent liquid passage therethrough, and second "open" sampling position oriented so as to reveal at least a portion of the lid opening;

biasing means connected to the closure disk, for urging the disk from the open position to the closed position;

an operable latch connected to the lid and operable between an engaged position holding the disk in the open position against the force of the biasing means, and a disengaged position out of contact with the disk permitting the disk to rotate to the closed position;

a trigger connected to the lid, operable between a first position retaining the latch in the engaged position and a second position releasing the latch from the first trigger position;

a screen projecting upwardly from a top surface of the lid, surrounding the lid opening; and a cover extending across an upper end of the screen to secure the screen and enclose the lid opening within the perimeter of the screen.

16. A liquid sample collection apparatus, comprising:

a sample container having an open mouth at an upper end for collecting a liquid sample;

a lid removably connected to the container mouth, for selectively closing the container mouth;

said lid having an opening therethrough for the passage of liquid sample into the container;

a closure disk operably connected to the lid for movement between a first "closed" position covering the lid opening to prevent liquid passage therethrough, and a second "open" sampling position oriented so as to reveal at least a portion of the lid opening;

biasing means connected to the closure disk, for urging the disk from the open position to the closed position;

an operable latch connected to the lid and operable between an engaged position holding the disk in the open position against the force of the biasing means, and a disengaged position out of contact with the disk permitting the disk to rotate to the closed position;

a trigger connected to the lid, operable between a first position retaining the latch in the engaged position and a second position releasing the latch from the first trigger position;

a ground engaging support post for supporting the container at a predetermined level relative to the ground; and a holder adjustably mounted on the post for selective vertical adjustment along the post, said container removably secured in said holder.

17. The apparatus of claim 16, wherein the holder includes a frame with upper and lower ends, the upper end open to selectively receive the container, and the lower end including a bottom to support a lower end of the container, said frame adjustably mounted on the post to retain the container in an upright orientation and further comprising means for selectively securing the container within the holder to prevent upwardly movement of the container out of the upper end of the holder.

18. The apparatus of claim 17, wherein said frame includes an operable clamp adjustably securing the holder to the post, the clamp operable between a "clamped" position selectively securing the holder in the desired position on the post and an "unclamped" position, permitting vertical movement of the holder along the post.

* * * * *